United States Patent
Dekker et al.

(10) Patent No.: US 11,407,008 B2
(45) Date of Patent: Aug. 9, 2022

(54) ULTRASOUND TRANSDUCER ASSEMBLY AND METHOD FOR MANUFACTURING AN ULTRASOUND TRANSDUCER ASSEMBLY

(71) Applicant: KONINKLIJKE PHILIPS N.V., Eindhoven (NL)

(72) Inventors: Ronald Dekker, Eindhoven (NL); Vincent Adrianus Henneken, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1320 days.

(21) Appl. No.: 14/913,402

(22) PCT Filed: Aug. 14, 2014

(86) PCT No.: PCT/EP2014/067377
§ 371 (c)(1),
(2) Date: Feb. 22, 2016

(87) PCT Pub. No.: WO2015/028311
PCT Pub. Date: Mar. 5, 2015

(65) Prior Publication Data
US 2016/0207068 A1   Jul. 21, 2016

(30) Foreign Application Priority Data
Aug. 26, 2013   (EP) .................................. 13181702

(51) Int. Cl.
*A61B 8/12*   (2006.01)
*A61B 8/00*   (2006.01)
(Continued)

(52) U.S. Cl.
CPC .............. *B06B 1/0607* (2013.01); *A61B 8/12* (2013.01); *A61B 8/4209* (2013.01);
(Continued)

(58) Field of Classification Search
CPC ... H01L 41/00–47; H01L 2224/75347–75349;
(Continued)

(56) References Cited

U.S. PATENT DOCUMENTS 5,640,371 A * 6/1997 Schmidt ................ B06B 1/0633
367/153
5,685,311 A * 11/1997 Hara ........................ A61B 8/12
600/393

(Continued)

FOREIGN PATENT DOCUMENTS

WO   2012066430 A1   5/2012

OTHER PUBLICATIONS

Khuri-Yakub et al "Miniaturized Ultrasound Imaging Probes Enabled By CMUT Arrays With Integrated Frontend Electronic Circuits" Conf. Proc. IEEE Eng. Med. Biol. Soc. 2010 1 p. 5987-5990.
(Continued)

*Primary Examiner* — Ashley K Buran
*Assistant Examiner* — Farouk A Bruce

(57) ABSTRACT

The present invention relates to an ultrasound transducer assembly (10), in particular for intra vascular ultrasound systems. The assembly (10) comprises a transducer array (12) including a plurality of transducer elements (14) for transmitting and receiving ultrasound waves. Two support elements (16, 18) are provided for supporting the transducer array (12) in a curved or polygonal shape. The support elements (16, 18) are connected via a flexible connection layer (20) to the transducer array (12) for flexibly connecting the support elements (16, 18) to the transducer array (12).

20 Claims, 8 Drawing Sheets

(51) Int. Cl.
 B06B 1/06 (2006.01)
 B06B 1/02 (2006.01)
 G10K 11/00 (2006.01)
 H01L 41/053 (2006.01)
 H01L 41/29 (2013.01)
(52) U.S. Cl.
 CPC .......... A61B 8/4483 (2013.01); B06B 1/0292 (2013.01); G10K 11/004 (2013.01); H01L 41/053 (2013.01); H01L 41/29 (2013.01)
(58) Field of Classification Search
 CPC ............... H01L 2224/76347–76349; H01L 2224/77347–77349; H01L 2224/78347–78349; H01L 2224/79347–79349; G10K 1/00–38; A61B 8/44–4494; H05K 2201/05–058
 See application file for complete search history.

(56) References Cited

U.S. PATENT DOCUMENTS

| | | | |
|---|---|---|---|
| 5,857,974 A * | 1/1999 | Eberle | B06B 1/0633 600/462 |
| 5,876,345 A * | 3/1999 | Eaton | A61B 8/12 600/463 |
| 6,049,958 A | 4/2000 | Eberle et al. | |
| 6,411,014 B1 * | 6/2002 | Toda | H04R 17/005 310/369 |
| 8,345,508 B2 | 1/2013 | Wodnicki | |
| 9,408,588 B2 | 8/2016 | Huang | |
| 2002/0093038 A1 * | 7/2002 | Ikeda | H04R 19/00 257/213 |
| 2005/0146247 A1 | 7/2005 | Fisher et al. | |
| 2005/0253484 A1 * | 11/2005 | Kishi | G02B 7/102 310/323.16 |
| 2005/0288587 A1 * | 12/2005 | Roh | A61B 8/00 600/445 |
| 2006/0103265 A1 * | 5/2006 | Miyoshi | B06B 1/0633 310/326 |
| 2006/0133198 A1 | 6/2006 | Fisher | |
| 2007/0066902 A1 * | 3/2007 | Wilser | A61B 8/445 600/459 |
| 2007/0264732 A1 | 11/2007 | Chen | |
| 2010/0262014 A1 * | 10/2010 | Huang | A61B 8/12 600/466 |
| 2010/0280388 A1 | 11/2010 | Huang | |
| 2011/0034809 A1 | 2/2011 | Eberle et al. | |
| 2013/0146995 A1 | 6/2013 | Chen | |
| 2013/0172756 A1 * | 7/2013 | Bruestle | G01S 15/8915 600/459 |
| 2013/0258814 A1 * | 10/2013 | Rich | B06B 1/0633 367/157 |

OTHER PUBLICATIONS

Wodnicki et al "Large Area MEMS Based Ultrasound Device for Cancer Detection" Nuclear Instruments and Methods in Physics Research, A 648 (2011) p. 135-138.
Kim et al, 2D Capacitive Micromachined Ultrasound Transducer Using Novel Tiling Based on Silicon Frame, Medical Imaging 2013: Ultrasonic Imaging Tomography and Therapy, Proc. of SPIE (2013) vol. 8675.
R. Dekker et al., "Living Chips and Chips for the Living," Proc. IEEE BCTM2012.
X. Cheng et al., "Fabrication and Assembly of a monolithic CMUT Array for Imaging Applications," Proc. IEEE Ultrasonics Symposium 2007.
J. Chen, et al., "Capacitive micromachined ultrasonic transducer arrays for minimal invasive medical ultrasound," J. Micromech. and Microeng., 20 (2010) 023001 (13pp).
B. Mimoun, V. Henneken, R. Dekker, "Flex-to-Rigid (F2R): A Novel Ultra-Flexible Technology for Smart Invasive Medical Instruments," Stretchable Electronics and Conformal Biointerfaces, edited by S.P. Lacour, S. Bauer, J. Rogers, B. Morrison (Mater. Res. Soc. Symp. Proc. vol. 1271E, Warrendale, PA, 2010), paper 1271-JJ05-09.

* cited by examiner

ULTRASOUND TRANSDUCER ASSEMBLY AND METHOD FOR MANUFACTURING AN ULTRASOUND TRANSDUCER ASSEMBLY

This application is the U.S. National Phase application under 35 U.S.C. § 371 of International Application No. PCT/EP2014/067377, filed on Aug. 14, 2014, which claims the benefit of EP Application No. 13181702.5 filed Aug. 26, 2013. These applications are hereby incorporated by reference herein.

FIELD OF THE INVENTION

The present invention relates to an ultrasound transducer assembly, in particular a capacitive micro-machined ultrasound transducer (CMUT) cell for intra vascular ultrasound transducer and a method of manufacturing the same. The present invention relates further to an ultrasound transducer.

BACKGROUND OF THE INVENTION

In the field of intra vascular ultrasound devices, it is generally known to mount an ultrasound transducer on the tip of a catheter to form a radial ultrasound image e.g. of a blood vessel or the surrounding tissue. The ultrasound transducer elements may be rotated in order to emit and receive ultrasound waves in a radial direction of the catheter tip.

It is further known to replace the mechanically scanning ultrasound transducer elements in the intra vascular ultrasound devices by electronically scanning devices having an annular array of ultrasound transducer elements. The ultrasound transducer elements used for the electronically scanning intra vascular ultrasound systems are usually based on ceramic piezo-electric material, wherein the fabrication of these devices is expensive and complex and the transducer elements cannot be scaled down to reduce the size of the intra vascular transducer.

Capacitive micro-machined ultrasound transducers (CMUT) are manufactured on the basis of a silicon wafer by means of IC process technologies and can be manufactured with low costs and can be scaled down to the dimensions of an intra vascular ultrasound transducer. For manufacturing an annular ultrasound transducer array, a semi-flexible ultrasound transducer array is formed on the basis of a silicon wafer substrate wrapped or bend around and attached to a cylindrically shaped submount structure in order to form the annular array and to transmit and receive ultrasound waves in the radial direction of a catheter.

A bendable micro machine ultrasound transducer array which can be attached to a cylindrical submount structure to form the cylindrically shaped ultrasound transducer array is known from US 2005/0146247 A2.

The submount structure for supporting the flexible ultrasound transducer array has to be fabricated with high precision and the mounting of the ultrasound transducer array on the submount structure is difficult and requires high precision alignment and complex handling equipment in order to produce the annular shaped ultrasound transducer array for intra vascular ultrasound systems.

WO 2012/066430 A1 discloses an ultrasound imaging apparatus suitable for minimally invasive ultrasound diagnostic devices in cardiac ablation monitoring and in tumor ablation monitoring, wherein the transducer assembly and the transducer system is manufactured on a patterned flexible foil by embedding transducer patches in apertures of the foil surface.

SUMMARY OF THE INVENTION

It is an object of the present invention to provide an improved ultrasound transducer assembly, in particular for intra vascular ultrasound systems having a reduced size and which can be produced precisely with low technical effort.

In a first aspect of the present invention, an ultrasound transducer assembly, in particular for intra vascular ultrasound systems is provided comprising:
a transducer array including a plurality of transducer elements for transmitting and receiving ultrasound waves,
two support elements flexibly connected to opposite sides of the transducer array for supporting the transducer array in a curved or polygonal shape, and
a flexible connection layer connected to the transducer array and to the support elements for flexible connecting the support elements to the transducer array.

In a further aspect of the present invention, a method for manufacturing an ultrasound transducer assembly, in particular for intra vascular ultrasound systems, is provided comprising the steps of:
providing a transducer array connected to a transducer support portion of a substrate,
connecting a flexible connection layer to the substrate,
separating a portion of the substrate from the transducer support portion to form a support element for supporting the transducer portion so that the support element is connected to the transducer portion via a flexible layer, and
bending the flexible connection layer to connect the support element to the transducer support portion.

In a still further aspect of the present invention, an ultrasound transducer, in particular for intra vascular ultrasound systems is provided, comprising an elongated probe including a tip and an ultrasound transducer that comprises an ultrasound transducer assembly of this kind.

Preferred embodiments of the invention are defined in the dependent claims. It should be understood that the claimed method has similar and/or identical preferred embodiments as the claimed device and as defined in the dependent claims.

The present invention is based on the idea to manufacture the transducer elements and the support elements in the same micro-fabrication process to reduce the manufacturing effort and to connect the transducer array and the support element via a flexible connection layer in the same manufacturing process so that the support elements and the transducer elements can be assembled to each other precisely with low technical effort. The ultrasound transducer assembly can be assembled by bending the support element via the flexible connection layer to the transducer array for supporting the transducer array in the curved or polygonal shape. Hence, the manufacturing effort is reduced since the support element and the transducer array are preassembled by means of the flexible connection layer and the precision of the assembling is increased, since the flexible connection layer connects the support element and the transducer array in a predefined position. Further, the size of the ultrasound transducer assembly can be reduced, since the transducer array and the support element can be manufactured in a micro-fabrication process.

In a preferred embodiment, the connection layer comprises electrical interconnects for electrically connecting the transducer elements to the support elements. This is a possibility to further reduce the manufacturing effort, since the electrical connection of the transducer elements is integrated in the transducer assembly.

In a further preferred embodiment, the support element comprises at least two electrical contact portions for electrically connecting the transducer assembly to a driver device. This is a possibility to connect the ultrasound transducer assembly with low technical effort to a driver device e.g. by means of a connector or a plug.

In a preferred embodiment, the support element comprises a support portion having a circular or polygonal shape. This is a possibility to define the outer form of the ultrasound transducer assembly and to support the transducer array in a predefined shape.

It is further preferred that the support element comprises a connection portion having a larger diameter than the support portion, wherein the connection portion is connected to the connection layer. Hence, the transducer array can be supported in a radial direction by means of the support portion and in an axial direction by means of the connection portion which has a larger diameter than the support portion so that the assembled ultrasound transducer assembly has a solid main body.

In a further preferred embodiment, the connection layer is connected to an end face of the support element. This is a possibility to further reduce the manufacturing effort, since the support element and the transducer array can be connected to a plane surface to the flexible connection layer.

In a further preferred embodiment, the support element comprises a central recess for supporting the ultrasound transducer assembly. This is a possibility to mount the transducer assembly coaxial to a catheter tip or the like by means of a single connection bolt connectable to the recess.

The ultrasound transducer assembly comprises two support elements flexible connected to opposite sides of the transducer array. This is a possibility to further improve the stability of the ultrasound transducer assembly since the transducer array can be supported at opposite sides.

In a preferred embodiment, the flexible layer is a polyimide layer or a parylene layer. This is a simple possibility to provide the flexible connection between the support element and the transducer array with low technical effort.

In a preferred embodiment, the assembly has a cylindrical or a multifaceted shape, wherein the transducer elements are disposed at a circumferential surface of the ultrasound transducer assembly in order to transmit and receive the ultrasound waves in a radial direction. This is a possibility to transmit and receive ultrasound waves in a radial direction and to combine the ultrasound transducer assembly with a catheter or the like to form an intra vascular ultrasound system.

In a preferred embodiment of the method for manufacturing an ultrasound transducer assembly, the substrate is covered by an etch mask at a surface opposite to the flexible layer. This is a possibility to separate the support element from the transducer array with low technical effort while the support element and the transducer array are still connected via the flexible layer.

In a preferred embodiment, the support element is separated by dry etching of the substrate. This is a simple solution to provide a support element having a precise and predefined shape with low technical effort.

It is further preferred that the ultrasound transducer assembly comprising the transducer array and the support element is separated from the substrate by dry etching of the substrate and by mechanically separating the flexible layer. This is a simple possibility to define the transducer assembly within the substrate and to extract the transducer assembly from the substrate with low technical effort by breaking the elements defined by the dry etching process out of the substrate.

As mentioned above, due to the flexible layer connecting the support element and the transducer array, the ultrasound transducer assembly can be assembled by bending the support element to the transducer array so that the transducer elements can be connected to the support element in a curved or polygonal shape. Since the transducer array and the support element are formed from a silicon substrate by means of a micro-fabrication process, the ultrasound transducer assembly can be scaled down and provided with small dimensions so that the ultrasound transducer assembly can be used for intra vascular ultrasound systems and can be manufactured with high precision and low technical effort.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
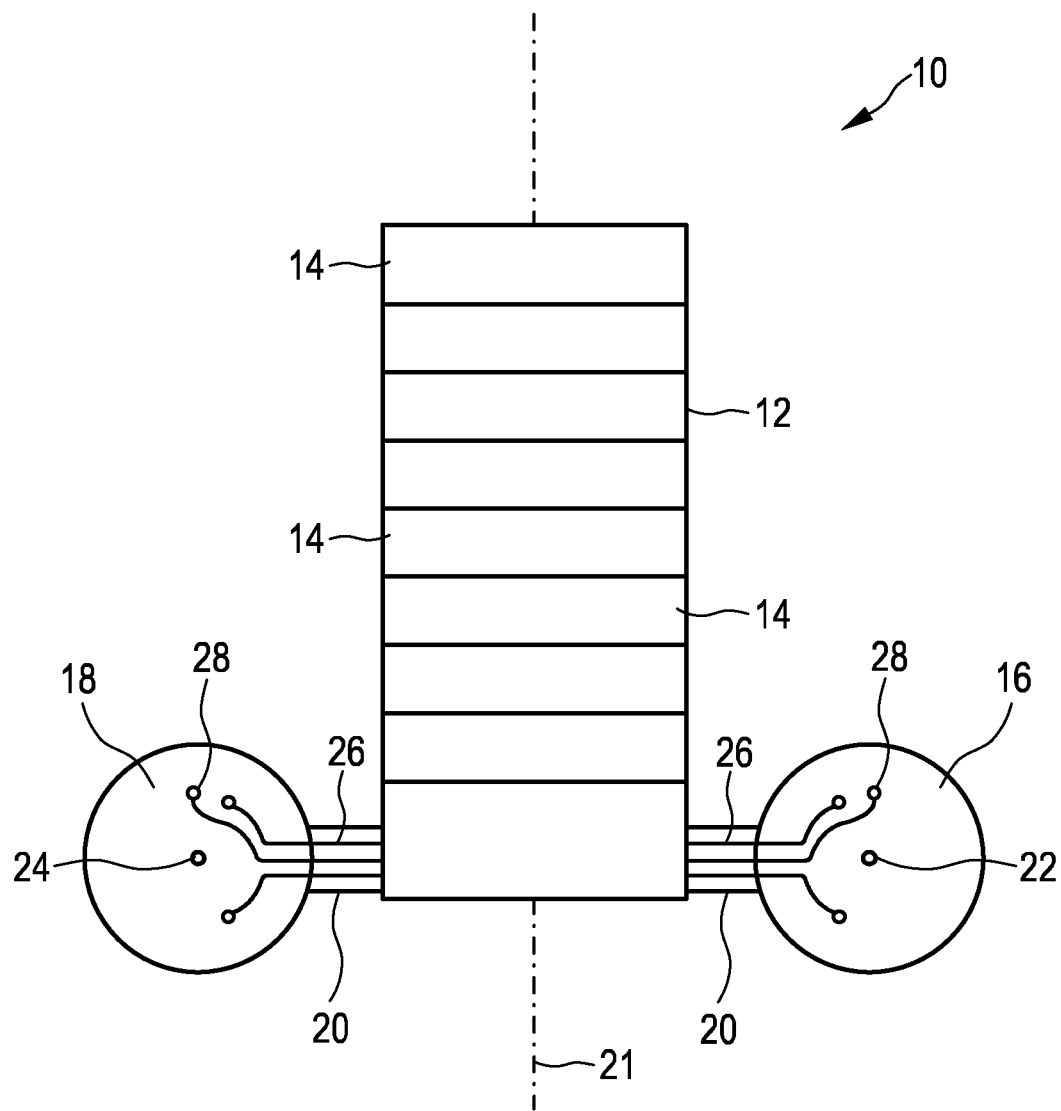
FIG. 1 shows a schematic drawing of an ultrasound transducer assembly in a plane view before assembling.

FIG. 1 shows a schematic top view of an ultrasound transducer assembly generally denoted by 10. The transducer assembly comprises a transducer array 12 including a plurality of transducer elements 14 for emitting and receiving ultrasound waves. The transducer assembly 10 comprises two support elements 16, 18 which serve as submount elements for the transducer array 12. The support elements 16, 18 have a circular shape and are connected to the transducer array 12 by means of a flexible connection layer 20. The transducer array 12 has an elongated shape in the direction of longitudinal axis 21.

The transducer elements 14 are formed as capacitive micro-machined ultrasound transducers (CMUT). The transducer elements 14 are flexibly connected to each other so that the transducer array 12 can be bent in order to form an annular, circular or polygonal transducer array 12 as described in the following. The transducer elements 14 can be flexibly connected to each other by means of a flexible layer, which may be connected in one piece to the connection layer 20.

The support elements 16, 18 each comprise a central recess 22, 24 or a central opening 22, 24 or a central hole 22, 24 in order to support the transducer assembly 10. The flexible connection layer 20 flexibly connecting the support elements 16, 18 to the transducer array 12 comprises integrated electrical interconnects 26 for electrically connecting the transducer elements 14 to the support elements 16, 18. Preferably, the electrical interconnects 26 are connected to electrical connection elements 28 or bond bads 28 formed at a surface of the support elements 16, 18 in order to electrically connect the transducer elements 14 to a driver device for driving the transducer array 12. Each of the transducer elements 14 may be connected to one connection element 28 of the first support element 16 and to one of the connector elements of the second support element 18 in order to drive each of the transducer elements 14 separately. The electrical interconnects 26 may be integrated in the connection layer 20 or may be printed on the connection layer 20.

The transducer assembly 10 is made from a silicon wafer by means of a micro-fabrication process using integrated circuit processing technology to form the transducer array 12 and the support elements 16, 18. The silicon wafer may be a blank wafer or may include preprocessed active devices or circuits like CMOS transistors.

The transducer elements 14, 18 may consist of silicon islands containing CMUT transducers connected to each other by means of the flexible connection layer 20.

The support elements 16, 18 are connected to the transducer array 12 by means of the flexible connection layer 20 so that the support elements 16, 18 can be bended by 90° so that the flexible transducer array 12 can be wrapped around the support element 16, 18 in order to form the transducer assembly 10 in a cylindrical form as further described in the following.

The embodiment shown in FIG. 1 comprises a linear array of transducer elements 14, however, any shape and any formation of transducer elements 14 is possible and can be used by the present invention, e.g. circular or polygonal transducer elements which are disposed in a one dimensional array or a two dimensional array including columns and rows of transducer elements 14 which may be alternatingly displaced.

Figure 2:
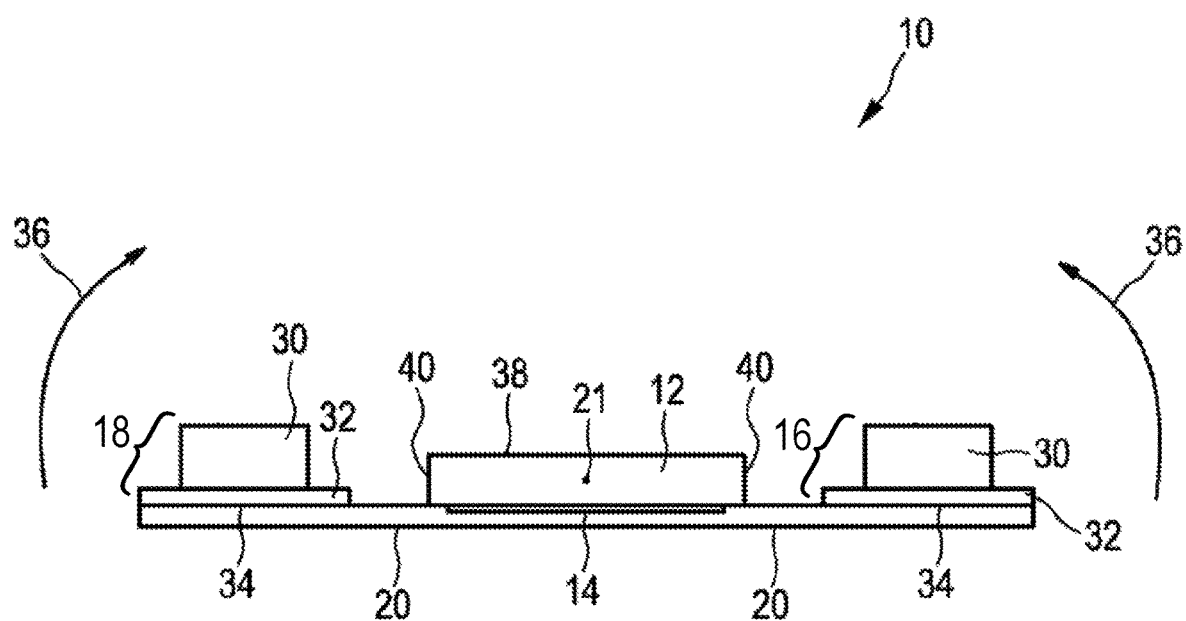
FIG. 2 shows a schematic drawing of the transducer assembly of FIG. 1 in a side view.

FIG. 2 shows a schematic diagram of the transducer assembly 10 in a side view along the longitudinal axis 21 of the transducer array 12. The transducer array 12 comprises the transducer elements 14 and is attached to the flexible connection layer 20, which is preferably formed as one piece. The support elements 16, 18 have a cylindrical shape including a support portion 30 and a connection portion 32, wherein the connection portion 32 has a larger diameter than the support portion 30. In other words, the support elements 16, 18 have a "champagne cork" shape. A base surface 34 or an end face 34 of each the connection portions 32 of the support elements 16, 18 are connected to the flexible connection layer 20. The support elements 16, 18 and the transducer array 16 are separated by a distance from each other and connected to each other only by means of the flexible connection layer 20.

In order to assemble the transducer assembly 10, the support elements 16, 18 are bended around the longitudinal axis 21 of the transducer array 12 as indicated by arrows 36.

In the fully assembled state, the circumferential surfaces of the support portions 30 are attached to a backside surface 38 of the transducer array 12 in order to support the transducer array 12 and to stabilize the form of the assembled transducer assembly 10. The connection portion 32 of the support elements 16, 18 abut at a side surface 40 of the transducer array 12 in order to support the transducer array 12 in the axial direction of the assembled transducer assembly 10.

Figure 3A:
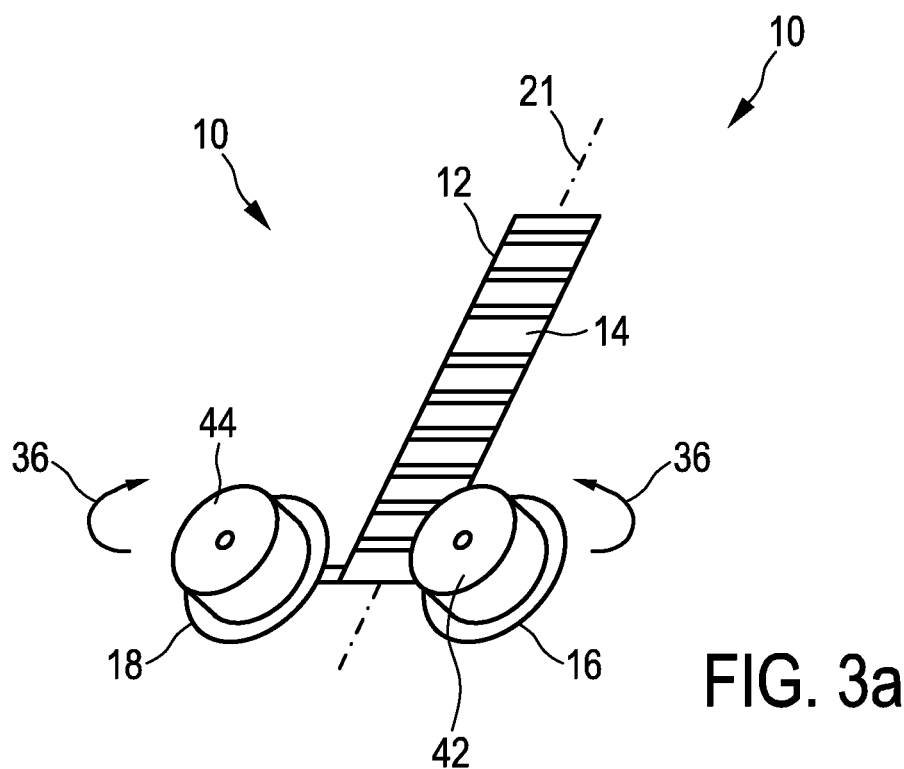
FIG. 3a, b show perspective views of the ultrasound transducer assembly for illustrating the assembling thereof.

FIG. 3a, b show schematic perspective views of the transducer assembly 10 to explain the assembling of the transducer assembly 10. Identical elements are denoted by identical reference numerals, wherein here merely the differences are explained in detail.

In a first step, the support elements are bended around the longitudinal axis 21 of the transducer array 12 so that inner end faces 42, 44 of the support elements 16, 18 may be attached to each other, e.g. by an adhesive or by soldering.

Figure 3B:
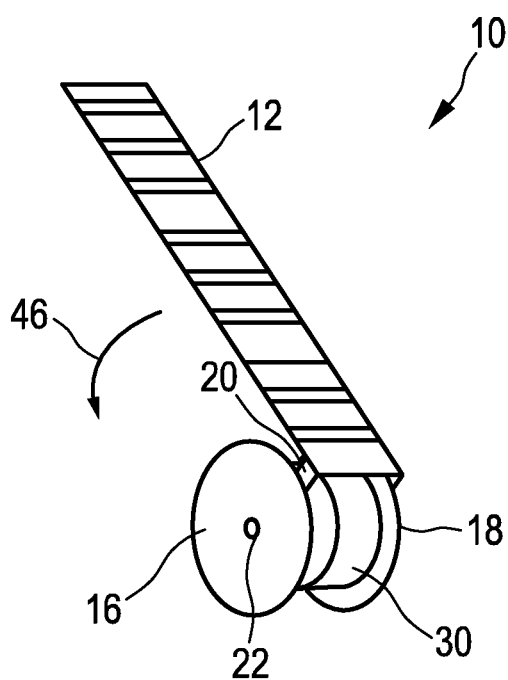

In FIG. 3b, the support elements 16, 18 are attached to each other at their inner end faces 42, 44 to form a cylindrical element to support the transducer array 12. The flexible transducer array 12 is bended as indicated by an arrow 46 and wrapped around the support portions 30 of the support elements 16, 18. Hence, in the assembled form, the transducer array 12 is attached radially to the support portions 30 and supported in an axial direction by means of the connection portions 32.

The inner end faces 42, 44 are connected to each other by means of an adhesive or soldering or the transducer array 12 is connected to the support portions by means of an adhesive, silicon rubber like PDMS or a heat shrinking tube.

The circumferential surface of the support portions 30 can have a circular or annular shape or may have a multi-faceted shape so that the assembled transducer assembly 10 and in particular the assembled transducer array 12 has a corresponding outer shape.

Figure 4:
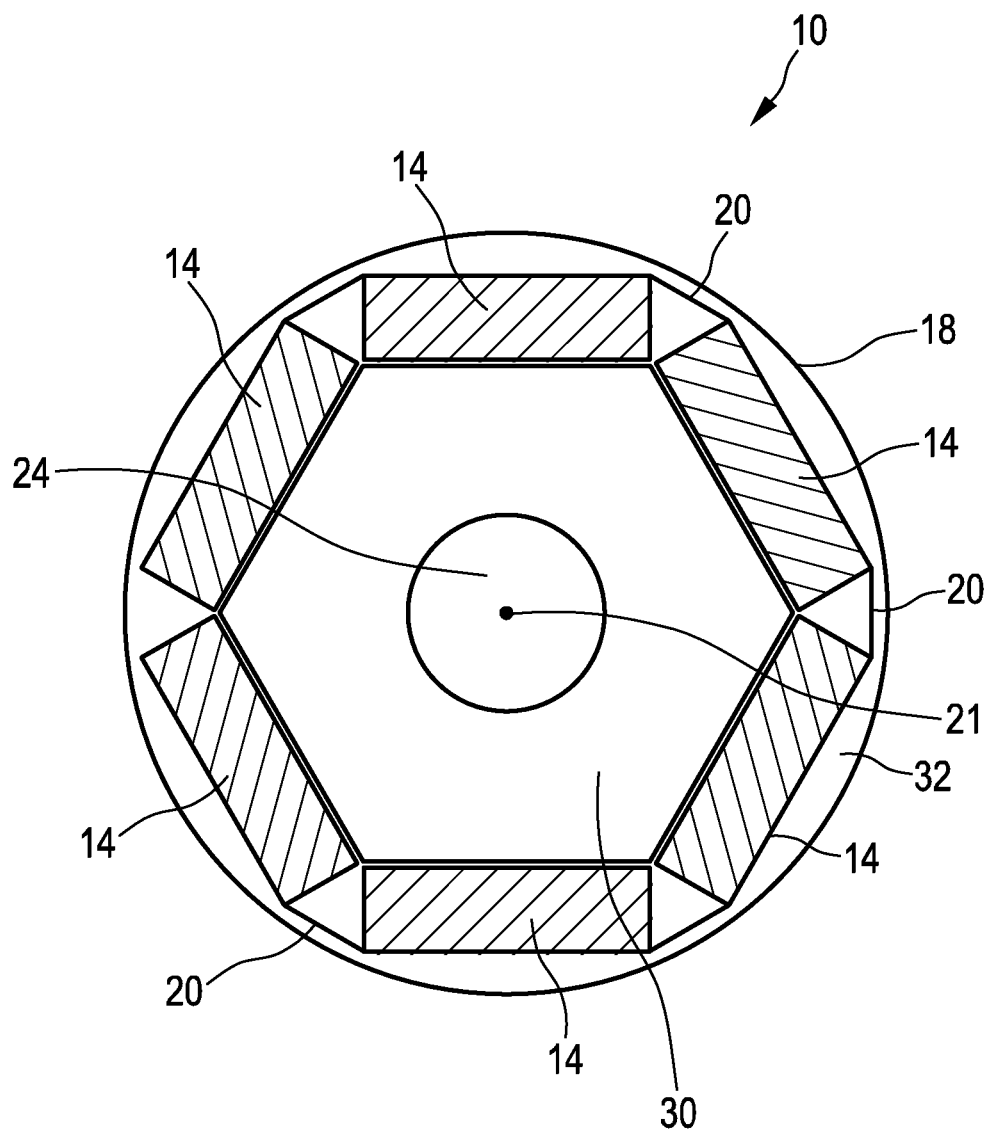
FIG. 4 shows a schematic cross section of the assembled ultrasound transducer assembly in an axial view.

FIG. 4 shows a schematic cross sectional view of the assembled transducer assembly 10 in an axial viewing direction.

The transducer elements 14 are wrapped around the multi-faceted support portion 30 of the support element 18 and respectively attached to the different faces of the support portion 30. The transducer elements 14 are flexibly connected to each other by means of the connection layer 20 which may be provided at the outside of the transducer array 12. By means of the so assembled transducer assembly 10, ultrasound waves can be transmitted and detected in a radial direction of the transducer assembly 10.

FIG. 5a-j show single method steps for manufacturing the transducer assembly 10. It is in general manufactured on a silicon wafer base by means of a micro-fabrication process.

Figure 5A:
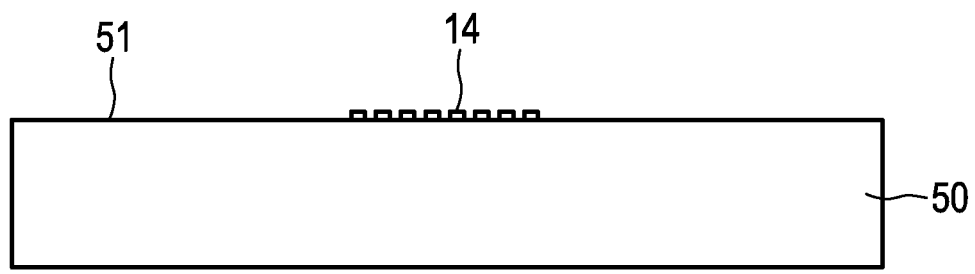
FIG. 5a-j show a sequence of manufacturing steps for manufacturing the ultrasound transducer assembly.

First, pre-processed transducer elements 14 are attached to a silicon wafer substrate 50. The substrate may be a fully processed wafer including active devices like CMOS transistors. The transducer elements 14 are attached to or formed at a front side 51 at the portion of the substrate 50 where the transducer array 12 will be formed as shown in FIG. 5a.

Figure 5B:
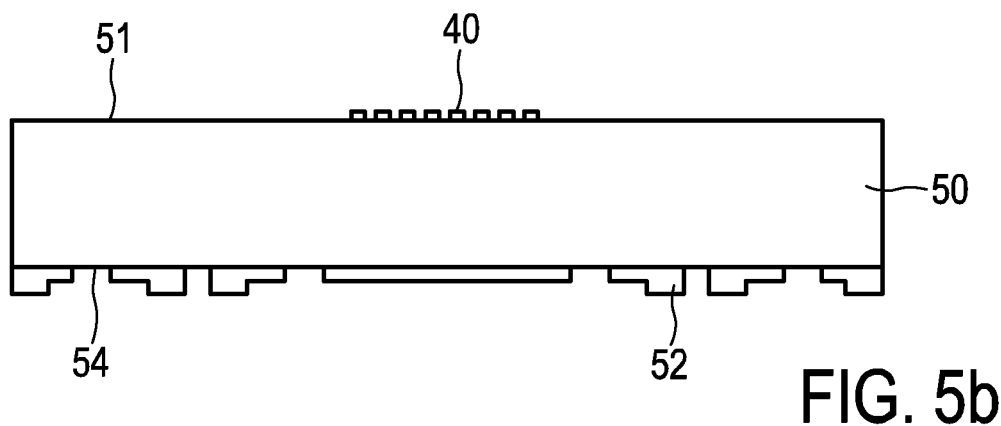

Further, a hardmask 52 is formed at a backside 54 of the substrate 50 by deposition and patterning of an oxide layer, e.g. a PECVD (plasma-enhanced chemical vapor deposition) oxide as shown in FIG. 5b.

Figure 5C:
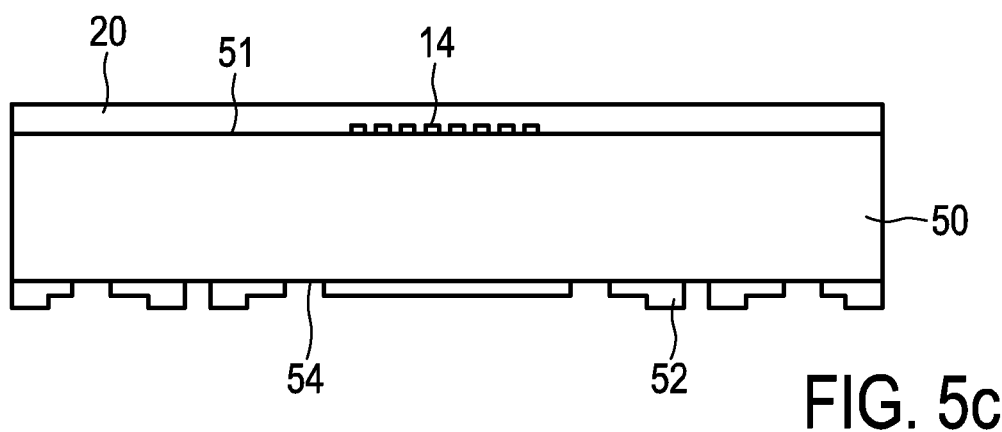

In the following step, the flexible connection layer 20 is formed at the front side 51 of the substrate 50 on the transducer elements 14 as shown in FIG. 5c. The flexible connection layer 20 is a polyimide flexible foil consisting of an aluminum re-routing layer sandwiched between two layers of polyimide of equal thickness. The flexible connection layer 20 may be a parylene layer.

Figure 5D:
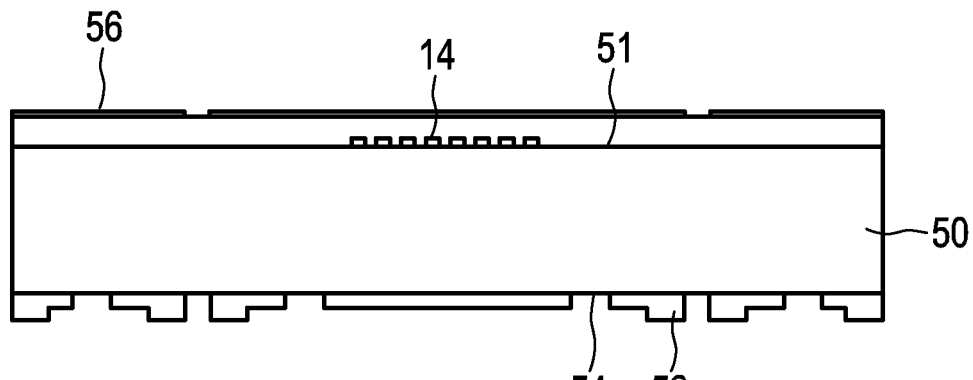

On the front side 51 of the substrate 50, a thin aluminum layer is deposited and patterned in order to form a hardmask 56 to structure the flexible connection layer 20 at the end of the process as shown in FIG. 5d.

Figure 5E:
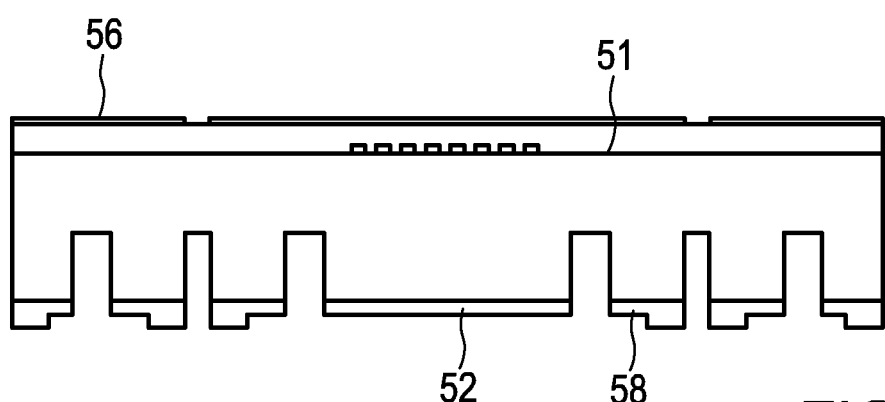
Figure 5F:
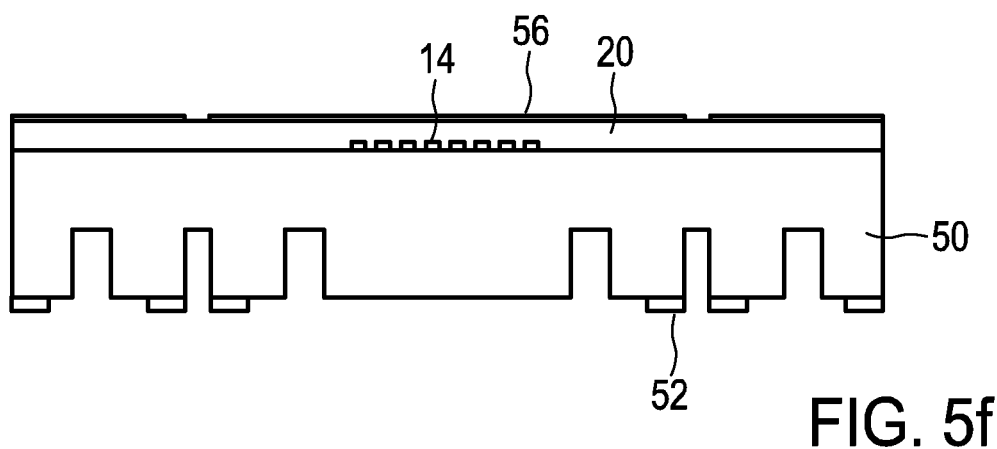

As shown in FIG. 5e, the backside 54 of the substrate 50 is etched by means of a dry-etching process to a depth of approximately 100 µm by using the hardmask 52. Further, a timed oxide etch process is used on the backside 54 of the substrate 50 in order to remove thinner portions 58 of the hardmask 52 as shown in FIG. 5f.

Figure 5G:
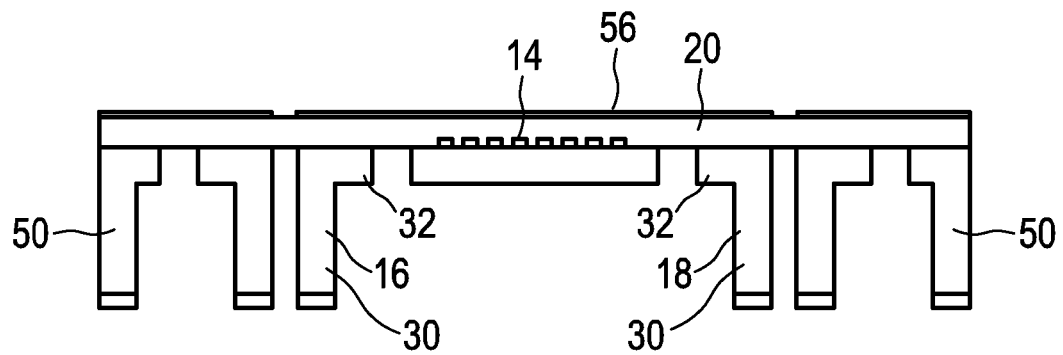

In a second dry etch process performed on the backside 54 of the substrate 50, the substrate 50 is partially etched down to the flexible connection layer 20 in order to separate the support elements 16, 18 from the transducer portion attached to the transducer elements 14. Due to the anisotropic dry etch process, the thickness of the transducer portion is reduced and a step is formed at the support elements 16, 18 forming the difference between the connection portion 32 and the support portion 30. As shown in FIG. 5g, after this etch process, the support elements 16, 18 are separated from the surrounding silicon substrate 50 and are merely connected to the surrounding substrate 50 by means of the flexible connection layer 20.

Figure 5H:
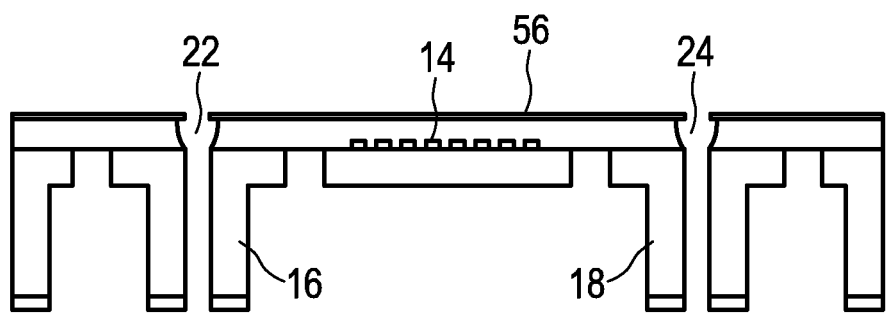
Figure 5I:
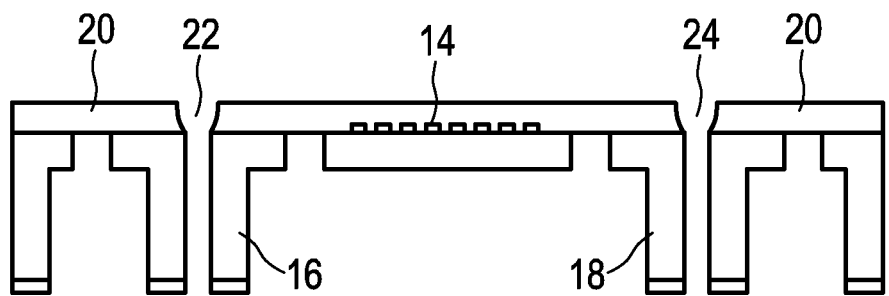

Using the aluminum layer 56 on the front side 51 of the substrate 50 as a hardmask, the flexible connection layer 20 is patterned by means of an oxygen plasma in order to form the recesses 22, 24, openings 22, 24 or the central holes 22, 24 in the support elements 16, 18 as shown in FIG. 5h. After the recesses or openings or holes 22, 24 are etched in the support element 16, 18, the hardmask 56 is removed by means of a timed wet etch as shown in FIG. 5i. At this stage of the process, the transducer assembly 10 is entirely structured and only supported within the substrate 50 by means of small tabs formed from flexible connection layer 20.

Figure 5J:
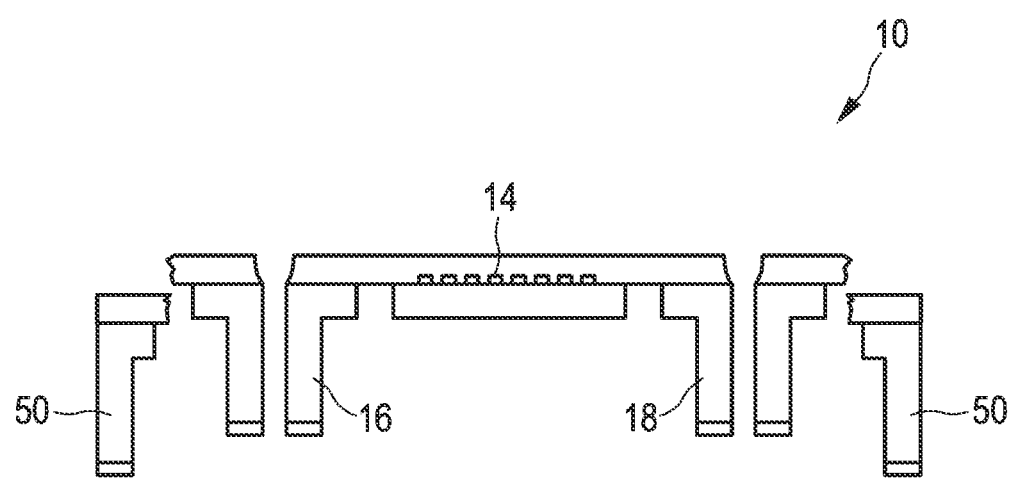

Finally, the transducer assembly 10 is removed from the substrate 50 by breaking the small flexible tabs 20 which is the only connection of the transducer assembly 10 to the substrate 50 as shown in FIG. 5j.

The overall height of the assembled transducer assembly 10 is limited to two times of the thickness of the substrate 50, however, by stacking a plurality of transducer assemblies 10 in a column, an ultrasound transducer system having an elongated shape can be formed having an arbitrary length.

The recesses 22, 24 or the openings 22, 24 or the holes 22, 24 may have a circular shape, a square shape, a triangular shape or a polygonal shape in order to prevent the rotation of the transducer assembly 10 connected to an ultrasound transducer system.

While the invention has been illustrated and described in detail in the drawings and foregoing description, such illustrations and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An ultrasound transducer assembly comprising:
   a transducer array including a plurality of transducer elements for transmitting and receiving ultrasound waves;
   two support elements, wherein each of the two support elements comprises an end face and a support portion; and
   a flexible connection layer connected to the transducer array and to the two support elements, wherein the two support elements are connected to the flexible connection layer on the opposite sides of the transducer array,
   wherein the flexible connection layer comprises two bends respectively at the opposite sides of the transducer array, wherein the two bends respectively orient the two support elements connected to the opposite sides of the transducer array such that the respective end faces of the two support elements are in direct physical contact with one another and the respective support portions of the two support elements are joined to form a combined support portion having a closed circular or polygonal shape, and
   wherein a region of the flexible connection layer connected to the transducer array is wrapped around a perimeter of the closed circular or polygonal shape of the combined support portion such that the region of the flexible connection layer connected to the transducer array surrounds a location of the combined support portion where the respective end faces of the two support elements are in direct physical contact, wherein the region of the flexible connection layer connected to the transducer array is different than the two bends.

2. The ultrasound transducer assembly as claimed in claim 1, wherein the flexible connection layer comprises electrical interconnects for electrically connecting the transducer elements to the support elements.

3. The ultrasound transducer assembly as claimed in claim 1, wherein each support element comprises at least one electrical contact portion for electrically connecting the ultrasound transducer assembly to a driver device.

4. The ultrasound transducer assembly as claimed in claim 1, wherein each support element comprises a connection portion having a larger diameter than the support portion, wherein the connection portion is connected to the flexible connection layer.

5. The ultrasound transducer assembly as claimed in claim 1, wherein the flexible connection layer is connected to the respective end faces of the two support elements.

6. The ultrasound transducer assembly as claimed in claim 1, wherein each support element comprises a central recess for supporting the ultrasound transducer assembly.

7. The ultrasound transducer assembly as claimed in claim 1, wherein the flexible connection layer is a polyimide layer or a parylene layer.

8. The ultrasound transducer assembly as claimed in claim 1, wherein the ultrasound transducer assembly has a cylindrical or multifaceted shape, wherein the transducer elements are disposed at a circumferential surface of the ultrasound transducer assembly in order to transmit and receive the ultrasound waves in a radial direction.

9. An ultrasound transducer apparatus, comprising an elongated probe including a tip and the ultrasound transducer assembly as claimed in claim 1 for emitting and detecting ultrasound waves in a radial direction of the elongated probe.

10. The ultrasound transducer assembly of claim 1, wherein the flexible connection layer comprises a first side and an opposite second side, wherein the first side of the flexible connection layer is wrapped around the perimeter of the closed circular or polygonal shape on a first of the two support portions, and wherein the second side of the flexible connection layer is wrapped around the perimeter of the closed circular or polygonal shape on a second of the two support portions.

11. The ultrasound transducer assembly of claim 1, further comprising a substrate, wherein the transducer array is disposed on the substrate, and wherein the two support elements are formed from the substrate.

12. The ultrasound transducer assembly of claim 11, wherein the substrate comprises transistors.

13. The ultrasound transducer assembly of claim 11, wherein the transducer array is formed on the substrate.

14. The ultrasound transducer assembly of claim 11, wherein the substrate comprises a silicon wafer.

15. The ultrasound transducer assembly as claimed in claim 1, wherein each of the two respective end faces is perpendicular to the respective closed circular or polygonal shape.

16. A method for manufacturing an ultrasound transducer assembly in particular for intra vascular ultrasound systems, comprising the steps of:
providing a transducer array disposed on a transducer portion of a substrate;
connecting a flexible connection layer to the substrate;
separating a portion of the substrate from the transducer portion to form two support elements for supporting the transducer portion so that the two support elements are connected to opposite sides of the transducer array via the flexible connection layer, wherein each of the two support elements comprises an end face and a support portion; and
bending the flexible connection layer at the opposite sides of the transducer array to respectively orient the two support elements connected to the opposite sides of the transducer array such that the respective end faces of the two support elements are in direct physical contact with one another and the respective support portions of the two support elements are joined to form a combined support portion having a closed circular or polygonal shape; and
wrapping a region of the flexible connection layer connected to the transducer array around a perimeter of the closed circular or polygonal shape of the combined support portion such that the region of the flexible connection layer connected to the transducer array surrounds a location of the combined support portion where the respective end faces of the two support elements are in direct physical contact, wherein the region of the flexible connection layer connected to the transducer array is different than the bending in the flexible connection layer at the opposite sides of the transducer array.

17. The method as claimed in claim 16, wherein the substrate is covered by an etch mask at a surface opposite to the flexible connection layer.

18. The method as claimed in claim 16, wherein the support elements are separated by dry etching of the substrate.

19. The method as claimed in claim 16, wherein the ultrasound transducer assembly including the transducer array and the support elements are separated from the substrate by dry etching of the substrate and by mechanically separating the flexible connection layer.

20. The method as claimed in claim 16, wherein providing the transducer array comprises at least one of:
forming the transducer array on the transducer portion of the substrate; or
connecting the transducer array to the transducer portion of the substrate.

* * * * *